United States Patent [19]

Slocum

[11] Patent Number: Plant 5,794

[45] Date of Patent: Oct. 28, 1986

[54] LOTUS PLANT CV CHARLES THOMAS

[76] Inventor: Perry D. Slocum, 191 Leatherman Gap Rd., Franklin, N.C. 28734

[21] Appl. No.: 789,131

[22] Filed: Oct. 18, 1985

[51] Int. Cl.[4] ..... A01H 5/00

[52] U.S. Cl. ..... Plt./68

[58] Field of Search ..... Plt./68

*Primary Examiner*—Robert E. Bagwill

[57] ABSTRACT

A novel lotus plant characterized by rose pink blossoms and small leaves borne on short petioles.

4 Drawing Figures

The present invention relates to a new and distinct variety of lotus plant named Charles Thomas of the decorative class which was originated by Perry D. Slocum, by crossing a *Nelumbo nucifera* variety: Shirokunshi with a *Nelumbo nucifera,* variety Rubrum.

The primary objective of this breeding was to produce a new and improved lotus variety having a new and colorful flower with a relatively short leaf growth which would be ideal for small pools. This objective was achieved along with other desirable improvements as evidenced by the unique combination of characteristics which are outstanding in the new variety and which distinguish it from all other lotus varieties by its:

(1) flowers of rose pink color;
(2) relatively short leaf growth;
(3) relatively small leaves; and
(4) folded and curled inner row of petals.

Asexual reproduction of the new variety which was performed at Franklin, N.C., by tuber division shows that the foregoing characteristics and distinctions come true to form and are established and transmitted through succeeding propagations.

The accompanying photographs show typical specimens of the leaf, stem, bud and flowers of the new lotus variety in different stages of development and as depicted in color as nearly true as is reasonably possible to make the same in color photographs of this character.

The following is a detailed description of the new variety, with color terminology in accordance with *Exotica,* 8th Edition, published by Roehrs Company, Inc. of New Jersey, Horticultural Color Guide:

Parentage: Seedling.
- *Seed parent.*—*Nelumbo nucifera,* variety: Shirokunshi.
- *Pollen parent.*—*Nelumbo nucifera,* variety: Rubrum.

Classification: Decorative.

Height: 2½ to 3 feet leaf height above water with flower approximately 10 inches above leaf.

Location where grown and observed: Outdoors in water pools in Franklin, N.C. from June through August.

Cold resistance: Hardy perennial.

Blooming period: In Franklin, N.C. climatic area, blooming begins in June and continues through August.

SEED POD

Figure 4:
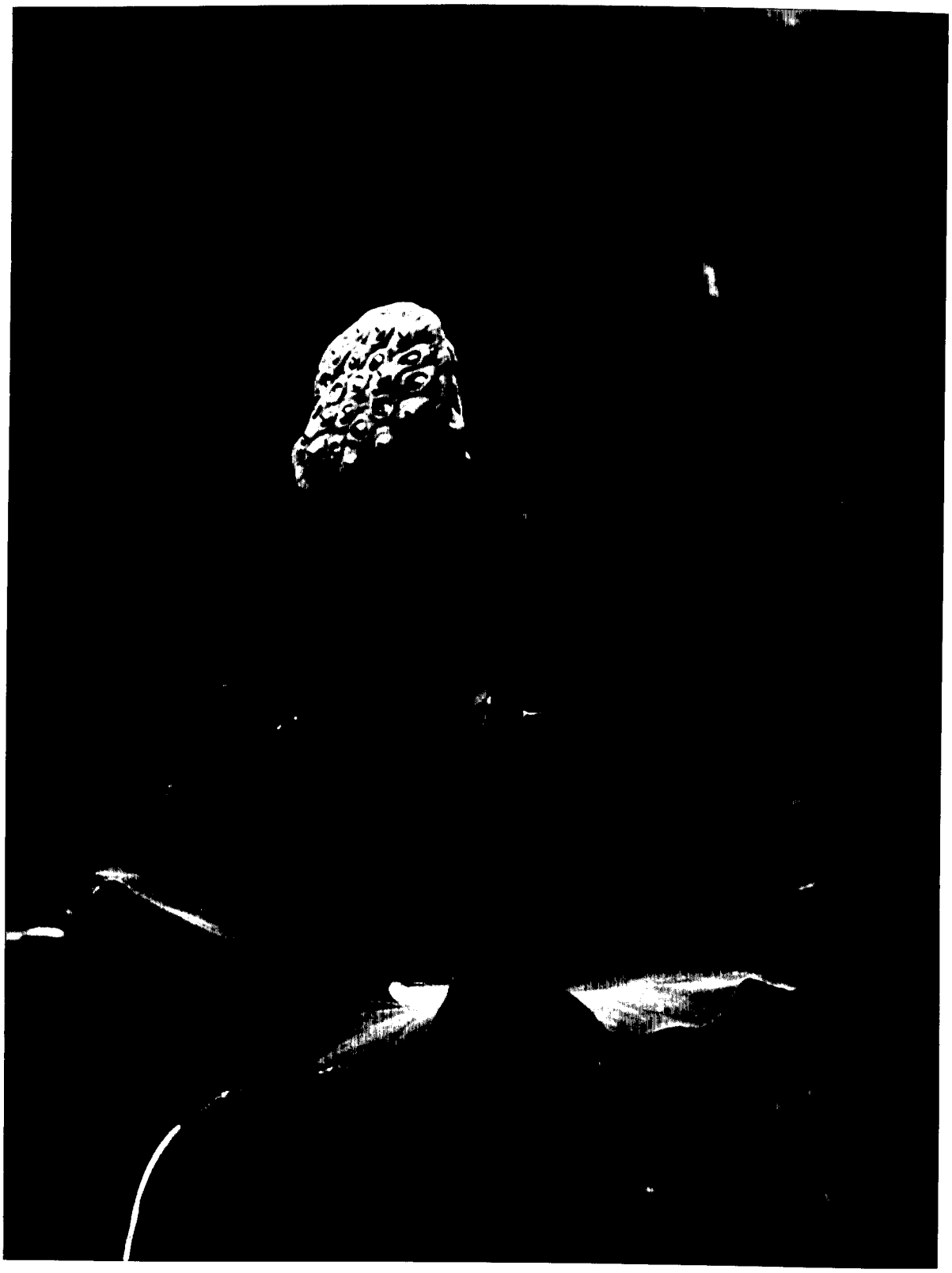

See FIG. 4 (non-distinctive) approximately 10–12 inches above leaf and having a somewhat conical appearance with the larger end approximately 2 inches in diameter.

FLOWER

Bud: Color as shown in FIG. 1, upper bud petals have #37 rose tips with #36 blush pine body portion, lower bud petals are generally lighter than #74 paris green with stem approximately #76 meadow green.

Figure 1:
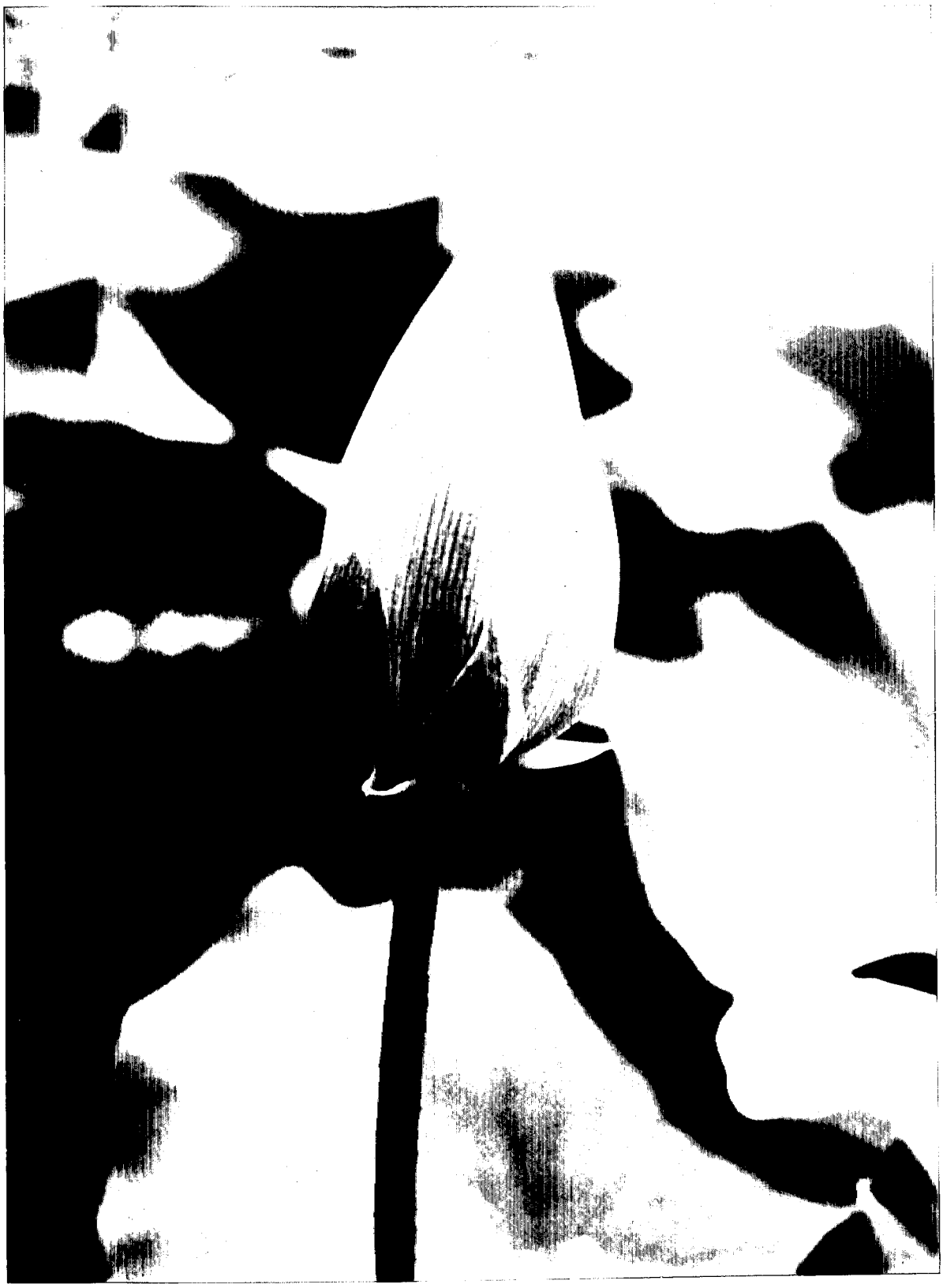
Figure 2:
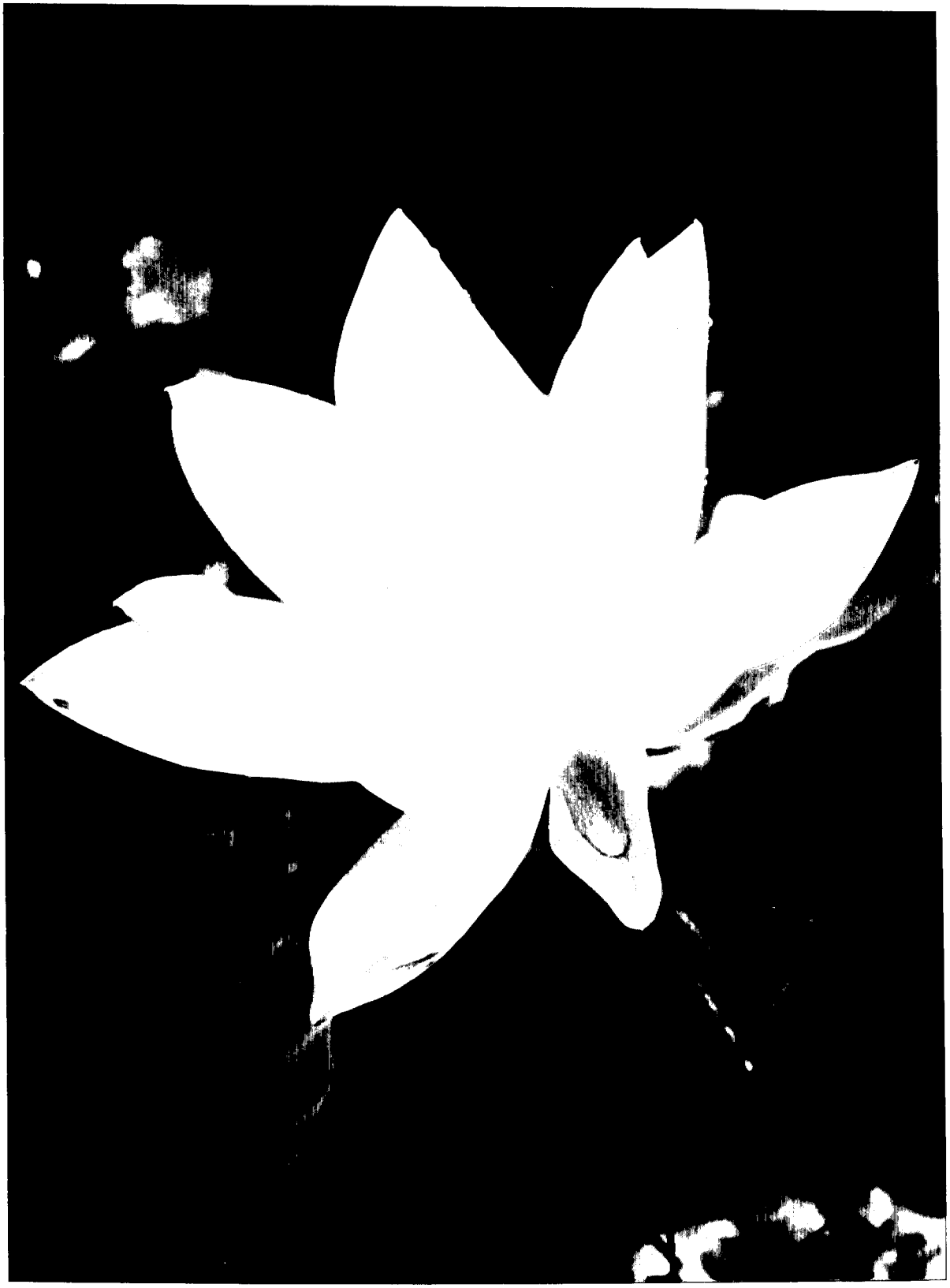

*When petals first divide.*—Upper petal tips are #37 rose pink with body portion being slightly darker than #36 blush pink, flushed with lighter than #74 paris green veins, lower petals are mostly lighter than #74 paris green tipped and bordered by #36 blush pink (see FIG. 1). When petals begin to unfurl the petal body portion is slightly darker than #36 blush pink (FIG. 2) with #38 rose tips.

Figure 3:
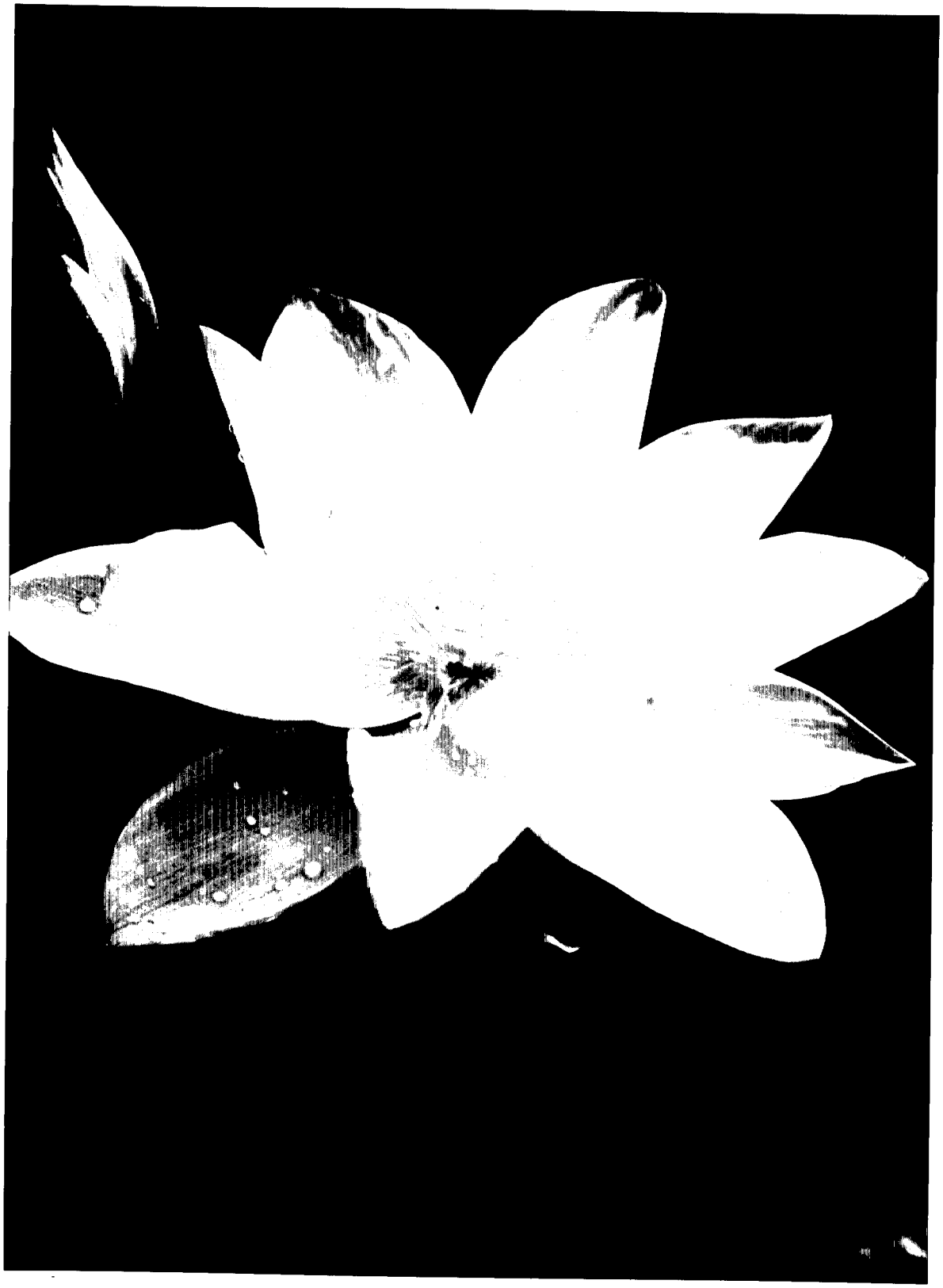

Bloom:
- *Size.*—7 to 9 inches in diameter (FIG. 3) with a height approximately 40 inches above the water.
- *Stem.*—Sturdy #76 meadow green color.
- *Form.*—Decorative cup shaped on 1st day; opening wide on 2nd and 3rd day.
- *Color.*—Center of flower — #1 cream pistil with #71 seafoam green border and #11 apricot stamens and anthers. Center petals — #38 rose with #39 purple towards the tips. Outer petals — #38 rose with #39 purple towards the tip.
- *Petals.*—Texture — smooth.
- *Fragrance.*—Characteristic lotus fragrance.

PLANT

Form: Branching is all done under water.

Growth: Small to medium leaf height approximately 2½ to 3 feet maximum above water and leaves are plentiful.

Foliage:
- *Size.*—12 to 15 inch diameter leaves (FIG. 4).
- *Quantity.*—Plentiful.
- *Color.*—#70 ivy green.
- *Texture.*—Medium thickness with smooth leaves.

The small to medium growth of this plants makes it ideal for an average water garden. The color of the flower is distinctively different from any other lotus by reason of its rich rose color.

I claim:

1. A new and distinct variety of lotus plant substantially as herein shown and described.

* * * * *